US007572780B2

(12) United States Patent
Hermsmeyer

(10) Patent No.: US 7,572,780 B2
(45) Date of Patent: Aug. 11, 2009

(54) METHOD AND KIT FOR REDUCING THE SYMPTOMS OF PERIPHERAL VASCULAR DISEASE

(75) Inventor: R. Kent Hermsmeyer, Portland, OR (US)

(73) Assignee: Dimera, Incorporated, Portland, OR (US)

( * ) Notice: Subject to any disclaimer, the term of this patent is extended or adjusted under 35 U.S.C. 154(b) by 554 days.

(21) Appl. No.: 10/348,570

(22) Filed: Jan. 21, 2003

(65) Prior Publication Data

US 2004/0142913 A1 Jul. 22, 2004

(51) Int. Cl.
*A61K 31/56* (2006.01)
(52) U.S. Cl. .......................... 514/177; 514/178
(58) Field of Classification Search ................. 514/177, 514/178
See application file for complete search history.

(56) References Cited

U.S. PATENT DOCUMENTS

| | | | |
|---|---|---|---|
| 4,196,188 A * | 4/1980 | Besins | 424/455 |
| 4,900,734 A | 2/1990 | Maxson et al. | |
| 5,422,119 A | 6/1995 | Casper | |
| 5,612,051 A | 3/1997 | Yue | |
| 5,859,001 A | 1/1999 | Simpkins et al. | |
| 5,891,462 A * | 4/1999 | Carrara | 424/449 |
| 5,968,918 A | 10/1999 | Kanda | |
| 5,985,861 A | 11/1999 | Levine et al. | |
| 5,998,638 A | 12/1999 | Bender | |
| 6,054,447 A | 4/2000 | Levine et al. | |
| 6,056,972 A | 5/2000 | Hermsmeyer | |
| 6,228,852 B1 | 5/2001 | Shaak | |
| 6,440,954 B1 | 8/2002 | Haber et al. | |
| 2002/0156090 A1 | 10/2002 | Day et al. | |

FOREIGN PATENT DOCUMENTS

| | | |
|---|---|---|
| DE | 3514724 A1 | 3/1986 |
| EP | 0 279 977 A2 | 8/1988 |
| EP | 0 399 432 A2 | 11/1990 |
| EP | 0754701 A1 | 1/1997 |
| WO | WO 95/07699 | 3/1995 |
| WO | WO 96/09826 | 4/1996 |
| WO | 97/46242 | 12/1997 |
| WO | 98/50042 | 11/1998 |
| WO | 98/50415 | 11/1998 |
| WO | 01/47451 A1 | 7/2001 |
| WO | 2004/019953 A1 | 3/2004 |
| WO | 2004/024206 A1 | 3/2004 |

OTHER PUBLICATIONS

Sitruk-Ware et al. "Oral micronized progesterone, bioavailability pharmaceutics, pharmaological and therapeutic implications,—a review," Contraception, 1987, vol. 36, No. 4, pp. 373-402.*
Ahrensfield, DC, et al, "How to Diagnose and Manage Occlusive Peripheral Arterial Disease", Women's Health in Primary Care, 1(6):500-507 (1998).
Mercuro, G, et al, "Effects of acute administration of natural progesterone on peripheral vascular responsiveness in healthy postmenopausal women", American Journal of Cardiology, 84(2):214-218 (1999) (Abstract Only).
Myers, Si, et al "Estrogen increases male rat aortic endothelial cell (RAEC) PGI2 release", Prostaglandins, 54(6):403-409 (1996).
White, MM, et al., "Estrogen, Progesterone, and Vascular Reactivity; Potential Cellular Mechanisms", Endocrine Review, 16(6):739-751 (1995).
Rylance, PB, et al., "Natural Progesterone and antihypertensive action", British Medical Journal, 290:13-14 (1985).
Miyagawa K., et al., "Medroxyprogesterone interferes with ovarian steroid protection against coronary vasospasm", Nature Medicine, 3(3):324-327 (1997).
Miyagawa K., et al., "$Ca^{+2}$ release mechanism of primate drug-induced coronary vasospasm", American Journal of Physiology, 272:H2645-H2654 (1997).
Jiang, C, et al., "Progesterone Induces endothelium-independent relaxation of rabbit coronary artery in vitro" European Journal of Pharmacology, 211:163-167 (1992).
Karmazyn, M. et al., "The Mechanism of Coronary Artery Spasm: Roles of Oxygen, Prostaglandins, Sex Hormones and Smoking", Medical Hypotheses, 5:447-452 (1979).
The Writing Group for the Pepi Trial, "Effects of Estrogen or Estrogen/Progestin Regimens on Heart Disease Risk Factors in Postmenopausal Women", Journal of American Medical Association, 273(3):199-208 (1995).
Ford, SP, et al., "Role of Estradiol-17β and Progesterone in Regulating Constriction of Ovine Uterine Arteries", Biology of Reproduction, 17:480-483 (1977).

(Continued)

Primary Examiner—Shengjun Wang
(74) Attorney, Agent, or Firm—Howard Eisenberg, Esq.

(57) ABSTRACT

A method for reducing the symptoms of peripheral vascular disease wherein a chemical agent that reduces peripheral vascular hyperreactivity in response to a stimulus for contraction of peripheral vascular musculature is administered to a subject in need thereof. Kits for administering the chemical agent to reduce the symptoms of peripheral vascular disease.

21 Claims, No Drawings

OTHER PUBLICATIONS

Hiatt, WR, "Medical Treatment of Peripheral Arterial Disease and Claudication", The New England J. of Med., 344:1608-1621 (2001).

Makin, AJ, et al., "ABC of Antithrombotic Therapy: Antithrombotic Therapy in Peripheral Vascular Disease", BMJ, 325:1101-1104 (Nov. 2002).

Bosch, JL, et al., "Health-related Quality of Life After Angioplasty and Stent Placement in Patients with Iliac Artery Occlusive Disease", Circulation, 99:3155-3160 (1999).

Moulds, RFW, et al., "The Effects of Platelet-Derived Contractile Agents on Human Digital Arteries", Clinical Science, 66:443-451 (1984).

Barbagallo, M., et al, "Vascular Effects of Progesterone, Role of Cellular Calcium Regulation," Hypertension, 37:142-147 (2001).

Barterlink, ML, et al, "The effects of single oral doses of 17B-estradiol and progesterone on finger skin circulation in healthy women and in women with primary Raynaud's phenomenon," Eur. J. Clin. Pharmacol., 46:557-560 (1994).

Dawson, DL, et al, "Peripheral arterial disease: Medical care and prevention of complications," Preventive Cardiology, 5:119-130 (2002).

Fraenkel, L, et al, "The association of estrogen replacement therapy and Raynaud's phenomenon in postmenopausal women," Annals Internal Medicine, 129(3):208-211 (1998).

Korting, GW, et al, "Gestagen-Behandlung der Sklerodermie," Aesth. Med., 16(10):291-294 (1967).

Pai, MP, et al, "Treatment of thrombo-angitis obliterans—a study of 74 cases," Antiseptic, 66(7):495-502 (1969).

Rosano, GMC, et al, "Comparative Cardiovascular Effects of Different Progestins in Menopause," Int. J. Fertil., 46 (5):248-256 (2001).

* cited by examiner

METHOD AND KIT FOR REDUCING THE SYMPTOMS OF PERIPHERAL VASCULAR DISEASE

FIELD OF THE INVENTION

The invention pertains to the use of therapeutic chemical agents to treat and/or prevent the symptoms of a medical condition. More particularly, the invention pertains to the use of therapeutic chemical agents to reduce the incidence and/or severity of the symptoms of peripheral vascular disease.

BACKGROUND

Peripheral vascular disease (PVD) is a serious medical condition that has been estimated to affect about 5% of people over the age of 50. The major clinical manifestations of PVD are those of ischemia and include pain, pallor, cramping, and loss of function of muscles, especially in the hands, feet, and legs. Severe cases of PVD can result in skin ulcerations or gangrene of an affected limb with the necessity of amputation.

The cause of PVD is a deficiency of blood supply to the peripheral circulation, that is to the arterial circulation supplying portions of the body other than the visceral organs, the brain, sensory organs such as the eye, and organs having specialized circulation such as the hypothalamus and pituitary. The peripheral circulation includes the circulation to the upper and lower extremities and, both in the extremities and in other portions of the body, to the skin, to skeletal muscle, and to bone.

PVD has been classified into two types of disorders, either functional or organic PVD. Functional peripheral vascular diseases lack an organic cause and do not involve defects in the structure of blood vessels. An example of a functional PVD is Raynaud's disease, which is a condition in which the small arteries that supply blood to the fingers and toes go into spasm when exposed to a stimulus such as cold. The term "Raynaud's disease" is used synonymously herein with "Raynaud's syndrome" and "Raynaud's phenomenon", and is referred to hereafter simply as "Raynaud's". The spasms of Raynaud's may also be induced by vibration, emotional upset, or cigarette smoking. Raynaud's is a common phenomenon, affecting millions of people in the United States alone. It may exist as a primary condition, that is with no associated disorder. Raynaud's may also occur as a secondary condition of other diseases such as scleroderma, lupus, or rheumatoid arthritis. There is no presently available treatment for functional PVD such as Raynaud's. Treatment for Raynaud's is aimed at removing the stimulus that causes the vasospasm. That is, affected people are instructed to avoid cold or other vasospasmogenic stimuli, to dress warmly, and to stop smoking.

Organic PVD is caused by structural changes in the blood vessels, such as inflammation, tissue damage, or the build-up of plaque. A functional PVD may exist as a component or as a contributory factor to organic PVD. An example of an organic PVD is intermittent claudication (IC). This condition, which has been estimated to affect up to 5% of men and 2.5% of women over the age of 60, is frequently due to atherosclerosis of the legs resulting in decreased blood supply. Typical symptoms of IC are cramping and intermittent pain in the legs and buttocks brought on by walking and which symptoms are relieved upon rest. If untreated, IC tends to progress and, if it becomes severe, may result in ulceration or gangrene of affected limbs, in extremely severe cases necessitating amputation. Treatment for IC includes treatment of any underlying heart disease, cessation of smoking, and the use of drugs, such as pentoxifylline and cilostazol, that prevent platelets from clotting together.

Other common causes of organic PVD include diabetes and thromboangiitis obliterans (TAO), also known as Buerger's Disease. Diabetes, due to an disorder in insulin production or secretion, is treated by administration of insulin and dietary regulation. TAO, an inflammation and thrombosis of arteries and vein in the hands and feet which is highly correlated to heavy cigarette smoking, is treated by cessation of smoking. Other therapies, such as the administration of anti-inflammatory and antithrombotic drugs, have not proven to be successful.

To date, no effective therapy exists for PVD, and no therapy exists for treating or reducing the incidence of functional PVD, whether the functional PVD exists alone or as a component or complicating factor of an organic PVD. Moreover, no therapy exists for long term administration to an individual who is susceptible to periodic episodes of symptoms due to PVD, such as to those suffering from Raynaud's.

DETAILED DESCRIPTION OF THE INVENTION

In one embodiment, the invention is a method for reducing the symptoms of peripheral vascular disease. In this specification, the term "reducing the symptoms" refers to reducing either or both of the incidence or severity of symptoms. According to this embodiment, a subject in need is administered a chemical agent that reduces hyperreactivity of peripheral vascular musculature in response to a stimulus for contraction. In a preferred embodiment, the chemical agent is a sex steroid hormone, selected from the group of an estrogen, an androgen such as testosterone, and a progestin, including the principal progestin, progesterone. In a most preferred embodiment, the sex steroid hormone is progesterone.

In another embodiment, the invention is a method to decrease peripheral vascular muscle hyperreactivity. According to this embodiment, a subject experiencing or susceptible to peripheral vascular muscle hyperreactivity is administered a chemical agent that reduces hyperreactivity of peripheral vascular musculature in response to a stimulus for contraction. In a preferred embodiment, the chemical agent is a sex steroid hormone, selected from the group of an estrogen, testosterone, and a progestin. In a most preferred embodiment, the sex steroid hormone is progesterone.

In another embodiment, the invention is a method to improve peripheral circulation by reducing vascular muscle hyperreactivity. According to this embodiment, a subject is administered a chemical agent that reduces hyperreactivity of peripheral vascular musculature in response to a stimulus for contraction. In a preferred embodiment, the chemical agent is a sex steroid hormone, selected from the group of an estrogen, an androgen such as testosterone, and a progestin. In a most preferred embodiment, the sex steroid hormone is progesterone.

In another embodiment, the invention is a kit for dispensing a pharmaceutical compound. According to this embodiment of the invention, the kit contains a package containing a pharmaceutical chemical compound that reduces hyperreactivity of peripheral vasculature and instructions for using the chemical compound to reduce the symptoms of PVD.

In accordance with the invention, a therapeutic chemical agent that reduces hyperreactivity of peripheral vasculature is administered to a subject or patient in need thereof. The term "hyperreactivity" as used herein means an abnormal tendency to experience a vasoconstriction or a vasospasm. A vasospasm is an inappropriate prolonged constriction of a blood vessel resulting from local vascular hyperreactivity to a vasoconstrictive stimulus, which constriction reduces blood flow to the area of the body served by the blood vessel and, if maintained for a sufficient length of time, results in symptoms of ischemia, such as pain, loss of function, or cell death. In the peripheral circulation, vasospasms may produce blanching of the skin, cold digits and, if severe, loss of function or even gangrene affecting the extremities. As used herein, the term "vasospasm" is defined as arterial constriction that persists for 5 minutes or more. Typically, such vasospasms are focal and constrict the diameter of the affected artery to 33% or less of control diameter in affected areas.

The therapeutic agent is administered for a time sufficient to reduce the symptoms of PVD and, preferably, is continued long-term for as long as needed to continue to reduce the symptoms of PVD. It is conceived that in many, if not all, cases the method of the invention will result in a symptomatic control, rather than a cure, of the symptoms of PVD. Consequently, it is conceived that in most cases the administration of a therapeutic agent to reduce the symptoms of PVD in accordance with the invention will be of long duration, lasting weeks, months, or even years.

The agent that is administered may be any agent that reduces peripheral vascular hyperreactivity. Such agents are distinguished from vasodilators, which dilate or reduce constriction of a blood vessel predominantly during the time that the vasodilator is present in sufficiently high concentration. Vasodilator reactivity, often referred to as vasodilator capacity or reserve, is distinct from hyperreactivity. In contrast to vasodilators, hyperreactivity reducing agents that are suitable for the invention are those that act over a prolonged time, that is such agents have a persistent action, and do not necessarily prevent a constriction which is not a vasospasm, but rather reduce the degree and/or duration of a vasoconstriction when the vessel is subject to a stress that would otherwise cause a persistent constriction. Such agents act by a genomic or non-genomic effect to reduce hyperreactivity. Included in the agents that are suitable for the invention are those chemical agents that, although not maintaining the diameter of a peripheral vessel at the pre-stimulus level, are effective in maintaining the vessel at a greater diameter when subjected to a vasospasmogenic stress than if the agent were not administered. Agents that reduce peripheral vascular hyperreactivity and also have vasodilator effects, such as progesterone, are included in those agents that are suitable for the invention.

In a preferred embodiment, the chemical agent that is administered is one or more of the sex steroid hormones selected from natural and synthetic estrogens, androgens, and progestins. Specific members of these classes of hormones are suitable for the invention if they are able, either alone or in combination with other sex steroid hormones or other chemical agents, to reduce the incidence or severity of peripheral vasospasms in response to a vasospasmogenic stimulus. It is conceived that estrogens that are suitable for the invention include estradiol and estriol. It is further conceived that androgens, such as testosterone and dihydroxytestosterone, are suitable for the invention. It is further conceived that progesterone is suitable for the invention and that many synthetic progestins will be found to be suitable for the invention. In a preferred embodiment, progesterone is the chemical agent that is administered in accordance with the invention, either alone or in combination with an androgen and/or an estrogen. Examples of other androgens and estrogens that are conceived to be suitable for the invention include those androgens and estrogens that are sold by and disclosed in a catalog of Steraloids, Inc. of Wilton, N.H., USA. Such estrogens include but are not limited to 3,17β.-estradiol (1,3,5(10)-estratriene-3,17β.-diol); 3,17α.-estradiol (1,3,5(10)-estratriene-3β.,17α.-diol); 3,17β.-estradiol 3-O-methyl ether (1,3,5(10)-estratriene-3,17β.-diol 3-O-methyl ether); 3,17α.-estradiol 3 acetate (1,3,5(10)-estratriene-3β.,17α.-diol 3-acetate); estrone (1,3,5(10)-estratriene-3-ol-17-one); estrone 3-O-methyl ether (1,3,5(10)-estratriene-3-ol-17-one 3-O-methyl ether); estriol (1,3,5(10)estratriene-3β., 16α., 17β.-triol); estriol 3-O-methyl ether (1,3,5(10)estratriene-3β, 16α., 17β.-triol 3-O-methyl ether); 17α.-ethynyl estradiol (1,3,5(10)-estratriene-17α.-ethynyl-3β., 17α.-diol); ethynyl estradiol 3-O-methyl ether (1,3,5(10)-estratriene-17α.-ethynyl-3β., 17α.-diol 3-O-methyl ether); 2-hydroxyestradiol (1,3,5(10)estratriene-2,3,17β,.-triol); and 2,3-methoxyestradiol (1,3,5(10)estratrien-2,3,17β.-triol 2,3-O-methyl ether) or estratriene-3-ol (1,3,5(10)estratrien-3-ol). Such estrogens may also include compounds that are estrogen beta-receptor agonists, such as androstane (5α-androstane-3β,17β-diol) or genistein. Such androgens include but are not limited to testosterone, dihydrotestosterone, methyltestosterone, oxandrolone, danazol, and fluoxymesterone.

Chemical agents that are suitable for the invention may be determined by testing prospective agents for the ability to reduce the incidence or severity of stress-induced peripheral vascular hyperreactivity. This information may be obtained in a variety of ways. For example, the chemical agents may be evaluated in vivo, either in a human or animal model, for their clinical effectiveness in reducing the incidence and/or the severity of stress-induced peripheral hyperreactivity. A patient who suffers from a PVD, such as Raynaud's, may be administered a test compound and then subjected to a stress that would typically result in a symptom of vascular hyperreactivity, such as cold. Absence or reduction in severity of the symptom indicates the effectiveness of the chemical agent and the suitability of the agent for the invention. Because treatment according to the invention is conceived to be a long-term prophylactic therapy, it is preferred that such testing be continued over an extensive period of time, with chronic application for several months or even several years, to determine long-term efficacy and the absence of undesirable side-effects. Additionally, it is preferred that such testing include a period when administration of the test compound is suspended to determine if symptoms of PVD return and then reinstituted to determine if the symptoms are once again managed by the test therapeutic compound.

A second example of a method for testing the suitability of a chemical compound for the invention is in vitro testing of the effect of a chemical compound on isolated peripheral arteries and/or on isolated peripheral vascular muscle cells (VMC) from peripheral arteries. The VMC are exposed to an agent known to induce peripheral vascular vasospasm, such as a physical stimulus such as cold or mechanical injury, or a chemical stimulus such as nicotine. Then, if the ability of a test compound to prevent vasospasms is to be determined, the VMCs are exposed to the test compound before the induction of vasospasms. If the ability of a test compound to treat, such as to relieve, an existing vasospasm is to be determined, the test compound is administered to the VMC following induction of a vasospasm. The VMCs are then observed for the presence or absence of indicia of vasospasm, such as shortening in length or increasing in cell width, changes in intracellular $Ca^{2+}$ levels, and changes in PKC signal intensity. See Hermsmeyer, U.S. Pat. No. 6,056,972, which is incorporated in its entirety herein by reference, for its disclosure of similar in vitro tests in isolated coronary arterial vascular muscle cells, which tests, although not necessarily the results, may be employed in studying the effects of chemical agents in controlling peripheral vascular vasospasms in response to vasospasmogenic stimuli.

The chemical agents, including sex steroid hormones, that are suitable for the invention act directly on the peripheral vascular musculature to reduce the incidence or severity of stress-induced vasospasm. Because of this, the method of the invention is applicable to any cause of peripheral vascular disease, especially functional peripheral vascular disease, whether primary or secondary. Examples of PVD of which the symptoms of which may be reduced, in accordance with the invention include Raynaud's, TAO, intermittent claudication, and PVD secondary to systemic illness such as diabetes, lupus, scleroderma, or atherosclerosis.

The dosage and frequency of administration of the chemical agent will vary depending on several factors including the particular chemical agent applied, the route of administration of the agent, and the severity of symptoms of PVD to which a subject is prone. Administration may be by any route by which chemical compounds are introduced into the body and by which such chemical compounds, or active metabolites thereof, reach peripheral vascular muscle cells in an effective concentration. Examples of suitable routes of administration are oral, nasal, alveolar aerosol, intraocular, oral palate, sublingual, transdermal, intradermal, and parenteral routes. Intravenous, intramuscular, and other injectable routes of administration are less preferred for long term therapy or prophylaxis.

Pharmaceutical compositions for use in accordance with the invention may conveniently be presented in unit dosage form and may be prepared by any of the methods well-known in the art of pharmacy. Such methods include the step of bringing the active agent into association with a carrier which constitutes one or more accessory ingredients. In general, the compositions are prepared by uniformly and intimately bringing the active compound into association with a liquid, solid, or semi-solid carrier, and then, if necessary, shaping a product. Formulations suitable for various modes of administering can be found in *Remington's Pharmaceutical Sciences*, Mack Publishing Co., 18th Edition, Easton, Pa., USA (1990), which is incorporated herein by reference.

Suitable delivery systems may include time-release, delayed release or sustained release delivery systems. Such systems avoid repeated administrations of the active compound, increasing convenience to the subject and the physician. Many types of release delivery systems are available and known to those of ordinary skill in the art. They include polymer base systems such as poly(lactide-glycolate), copolyoxalates, polycaprolactones, polyester amides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Patch technologies also can be used as a delivery system in accordance with the invention. Transdermal patches typically include a housing, a reservoir in the housing and a membrane attached to the housing adjacent the reservoir for placement against the epidermis of the human subject. The patch has also included an adhesive attached to the housing for holding the membrane to the epidermis of the subject. Patches capable of delivering a chemical agent according to the invention may be found in the following prior art patents: U.S. Pat. Nos. 3,731,683; 3,797,494; and 4,336,243; 4,628,052; 4,704,282; 4,788,062; 4,906,169; and 5,164,190, the disclosures of which are incorporated herein by reference.

Use of a long-term sustained release implant may be desirable. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention also includes various kits. Each of the kits includes a jar, tube, bottle, foil pouch, patch, or other container for holding a pharmaceutical preparation containing, as an active ingredient, a chemical compound for reducing the severity and/or incidence of symptoms of PVD and instructions for dispensing an amount of the pharmaceutical preparation effective to reduce symptoms of PVD. Alternatively, the kit may contain the chemical compound and a pharmaceutically acceptable carrier in separate containers, the contents of which are combined prior to administration.

Preferably, the pharmaceutical preparation is in the form of a topical preparation, either constructed and arranged to deliver an appropriate effective amount of the chemical compound or with a dispensing means permitting dispensing of appropriate amounts of the compound.

A topical preparation containing the chemical compound may be in the form of a cream, a lotion, an ointment, a gel, or other known forms for topical administration. If desired, the topical preparation may be contained in individual packets, each packet containing an appropriate dose for topical application. The kit may include a plurality of such packets, such as 30, 60, 100 or more packets, each packet containing an amount of cream that may be conveniently rubbed into a single location on the skin of a user, typically about 1-2 ml of the topical preparation.

Such cream, lotion, ointment, gel, or other form for topical administration may be administered such as by application, with or without rubbing, to the skin. One preferred location of administration is to the upper surface of the foot. Other examples of preferred locations for topical administration is to the skin of the face and of the hands and forearms.

One preferred formulation for chronic topical administration is as a transdermal patch. Such patches typically include a housing, a reservoir in the housing, a membrane attached to the housing, adjacent the reservoir, for placement against the epidermis of a human subject, and an adhesive attached to the housing for holding the membrane to the epidermis of the subject. A therapeutic chemical compound in a carrier is contained in the reservoir, and the patch is constructed and arranged to deliver an amount of the chemical compound to the epidermis of the subject to achieve effective blood levels of the compound to reduce the symptoms of PVD. Thus, the kits of the invention may utilize a transdermal patch as a means for both containing and the means for dispensing a metered amount of a medication for reducing the incidence and/or severity of symptoms of PVD.

The invention is described in further detail in the following non-limiting examples. In the examples, the invention is illustrated by use of the sex steroid hormones progesterone and testosterone. One skilled in the art will understand that the disclosure of these two hormones is merely illustrative and that the invention may be practiced with other sex steroid hormones and with chemical compounds other than sex steroid hormones as described above. Further, the invention is illustrated by showing the effects of medication to control the symptoms of Raynaud's. One skilled in the art will understand that Raynaud's is illustrative of PVDs and, because the physiology of peripheral vasospasm is similar in all cases of PVD, that the disclosure of Raynaud's is applicable to other causes of symptoms of PVD, especially those that include a functional PVD as the sole or contributory factor in the etiology of the symptoms.

EXAMPLE 1

VMC Preparation

Single VMCs from large arteries of the foreleg of adult rhesus monkeys are isolated and studied both as freshly dispersed and as primary cultures. The short-term primary cultured cells (never passaged) maintain the characteristics of the source tissue for 2 to 3 weeks, including contraction, relaxation, receptors, and membrane electrical properties. VMCs are dissociated with collagenase and protease enzymes in a potassium glutamate solution (KG) that prevents loading with $Na^+$, $Ca^{2+}$, or $Cl^-$ and results in a high proportion of viable, contracting cells. See, Self, D. A., et al., *J. Vasc. Res.* 31:359-366 (1994); and Rusch, N. J., et al., *Physiology and Pathophysiology of the Heart,* 999-1010 (1995), each of which is incorporated herein by reference. The cells prepared for culture are seeded at low density in cardiovascular culture solution for mammals, fifth generation (CV5M) on glass coverslips to facilitate selection of individual cells. VMCs are used for studies 7 to 14 days after attaching to coverslips.

EXAMPLE 2

Subcellular $Ca^2$ and PKC Localization

Freshly dispersed or primary cultured VMCs on glass coverslips are placed in a chamber of laminar flow design and observed with a high numerical aperture water immersion objective. Ionic solution for mammals version 2 (ISM2) is continuously pumped through the chamber (at 1 ml/minute) to provide continuous equilibration and washout of drugs. After a 15 minutes equilibration period, VMC are loaded for 15 minutes at room temperature with 3 μM fluo 3 (Molecular Probes, Inc.) for sensing $Ca^{2-}$ and for 10 minutes with 30-100 nM hypericin (LC Laboratories) for reporting PKC. Individual VMC are stimulated by adding 20 μl of 10 μM nicotine over the individual cell. After 15 seconds under no-flow conditions, continuous flow of ISM2 was reinstated and a chamber volume of approximately 300 μl was maintained. Fluorescent images are taken at 1, 2, 5, 10, 15, 20 and 30 minutes after stimulation for $Ca^{2+}$ and at 3, 4, 9, 16, 21 and 31 minutes for PKC to evaluate subcellular distribution of these signals, and to determine VMC contraction.

EXAMPLE 3

Drugs and Solutions

ISM2 contains (in mM): 100 NaCl, 4 $NaHCO_3$, 0.5 $NaH_2PO_4$, 4.7 KCl, 1.8 $CaCl_2$, 0.41 $MgSO_2$, 50 HEPES (pH 7.37), and 5.5 dextrose; KG solution contains (in mM): 140 K-glutamate, 16 $NaHCO_3$, 0.5 $NaH_2PO_4$, 30 HEPES, and 16.5 dextrose at pH 7.3. CV5M contains: 4.0 mM L-glutamine, 10 μg/ml ciprofloxacin (Miles Pentex/Bayer Corporation), 50 mM HEPES (pH 7.3), and 16 mM $NaHCO_3$ dissolved in 85% MEM-Earle's salts and 15% horse serum. Phenol red, known to have estrogenic activity, is omitted from all solutions.

One group of cells is pre-treated with a wash of 4 ng/ml of progesterone before stimulation with nicotine. A second group of cells is pre-treated with a wash of 4 ng/ml testosterone before stimulation. A third group of cells, the "non-treatment group", is pre-treated with a wash of normal saline before stimulation. A fourth group of cells, which forms the control group, is pre-treated with a wash of normal saline and followed by "stimulation" with normal saline.

EXAMPLE 4

Averaged $Ca^{2+}$ Signals

Normalized (per pixel) changes in intracellular $Ca^{2+}$ levels are expressed as averages over whole VMC and as peripheral-to-central ratios. After stimulation with nicotine, the non-treatment group of VMC show an immediate increase in whole cell $Ca^{2+}$ fluorescence followed by a slow, sustained increase (significantly different from control value at 1 minute and later). The peripheral-to-central ratio of $Ca^{2+}$ signal intensity decreases significantly at 5 minutes after stimulation. The ratio decreases because of $Ca^{2+}$ release from intracellular stores.

In contrast, VMC from progesterone or testosterone pre-treatment groups are only transiently stimulated by nicotine. $Ca^{2+}$ increases significantly over control only very early following the nicotine stimulation and with a smaller peak than in the non-treatment group. The decrease in peripheral-to-central $Ca^{2+}$ localization ratio is too small to be significant and is already reversed at 2 minutes.

EXAMPLE 5

Averaged PKC Signals

Whole cell PKC signals of VMC in the non-treatment group increase at central and peripheral loci after stimulation with nicotine, and continue to increase (significantly different from 0-minute control at 4 minutes and later). Peripheral-to-central PKC ratio decreases continuously and is significantly different from the progesterone and testosterone treatment groups at 16 minutes and subsequent times.

In progesterone and testosterone pre-treated VMC, stimulation with nicotine fails to change PKC loci or intensity significantly from control values, and peripheral-to-central PKC ratio is never significantly different from control.

EXAMPLE 6

Averaged Contractions

Normalized changes in cell widths from primary cultured VMC is determined. The width of VMC in all three non-control groups increases significantly at 3 minutes after stimulation with nicotine, demonstrating VMC contractions but of different magnitude. Contractions indicated by central cell widening are significantly different from 0-min controls in non-treatment VMC at 3 minutes and all subsequent times. Progesterone and testosterone treatment group VMC contractions are significantly different from 0-min controls only in the first few minutes following stimulation.

EXAMPLE 7

Treatment of Symptoms of PVD in Patients

An adult woman suffering from severe Raynaud's is treated by topically self-administering about 2 ml of a topical cream containing about 20 mg of progesterone per ml. This test is performed in order to determine the following: 1) whether the method of the invention would be successful in reducing the severity and/or incidence of the symptoms of PVD in a human suffering from PVD, 2) whether any beneficial effects would continue upon long-term therapy, 3) whether any deleterious effects would become evident upon long-term therapy, 4) whether symptoms would return upon cessation of treatment according to the invention, and 5) whether the method of the invention would be effective once again in reducing the severity or incidence of the symptoms of PVD upon re-commencement of therapy in accordance with the invention after symptoms had reappeared in their original incidence and/or severity.

The subject utilizes the progesterone cream by rubbing 2 ml of the cream into her skin daily for a period of over one year. The subject reports that symptoms of Raynaud's completely disappear during the period of treatment. The subject then ceases therapy for several weeks and reports that the symptoms of Raynaud's disease return and are severe. Therapy is recommenced once again and the subject reports that the symptoms of Raynaud's disease are controlled a second time as they had been during the initial period of therapy prior to the cessation of therapy.

The terms and expressions which have been employed in the foregoing specification are used as terms of description and not limitation, and there is no intention that the use of such terms and expressions excludes equivalents of the features shown and described above. Further modifications, uses, and applications of the invention described herein will be apparent to those skilled in the art. It is intended that such modifications be encompassed in the following claims.

The invention claimed is:

1. A method for reducing the symptoms of peripheral vascular disease (PVD) comprising administering to a subject in need thereof a progestin in an amount that is effective to reduce the incidence and/or severity of symptoms of PVD, thereby reducing the incidence and/or the severity of symptoms of PVD, wherein the progestin is administered by topical application to the skin in a composition in which progestin is the sole chemical agent that is effective in reducing the incidence and/or severity of symptoms of PVD.

2. The method of claim 1 wherein the PVD is selected from the group consisting of Raynaud's, intermittent claudication, thromboangiitis obliterans, and PVD secondary to diabetes, lupus, scleroderma, or atherosclerosis.

3. The method of claim 1 wherein the PVD is Raynaud's.

4. The method of claim 1 wherein the progestin is progesterone.

5. The method of claim 1 wherein the administration is oral.

6. The method of claim 1 wherein the topical application is by a cream, lotion, gel, or ointment.

7. The method of claim 1 wherein the topical administration is by a transdermal patch.

8. The method of claim 1 wherein the progestin is progesterone.

9. A method to decrease peripheral vascular muscle hyperreactivity comprising administering to a subject in need thereof a progestin in an amount that is effective to decrease peripheral vascular hyperreactivity, wherein the progestin is administered by topical application to the skin in a composition in which progestin is the sole chemical agent that is effective to decrease peripheral vascular hyperreactivity.

10. The method of claim 9 wherein the progestin is progesterone.

11. The method of claim 9 wherein the topical application is by a cream, lotion, gel, or ointment.

12. The method of claim 9 wherein the topical administration is by a transdermal patch.

13. The method of claim 9 wherein the progestin is progesterone.

14. A method to improve peripheral circulation by reducing vascular muscle hyperreactivity comprising administering to a subject in need thereof a progestin in an amount that is effective to improve peripheral circulation by reducing vascular muscle hyperreactivity, wherein the progestin is administered by topical application to the skin in a composition in which progestin is the sole chemical agent that is effective to improve peripheral circulation by reducing vascular muscle hyperreactivity.

15. The method of claim 14 wherein the subject is suffering from a peripheral vascular disease (PVD).

16. The method of claim 15 wherein the PVD is selected from the group consisting of Raynaud's, intermittent claudication, thromboangiitis obliterans, and PVD secondary to diabetes, lupus. sclerodermia, or atherosclerosis.

17. The method of claim 16 wherein the PVD is Raynaud's.

18. The method of claim 14 wherein the progestin is progesterone.

19. The method of claim 14 wherein the topical application is by a cream, lotion, gel, or ointment.

20. The method of 14 wherein the topical administration is by a transdermal patch.

21. The method of claim 14 wherein the progestin is progesterone.

* * * * *